United States Patent [19]

Houlihan et al.

[11] Patent Number: 4,670,600

[45] Date of Patent: Jun. 2, 1987

[54] PREPARATION OF SUBSTITUTED AMINES

[75] Inventors: William J. Houlihan, Mt. Lakes, N.J.; Paul G. Mattner, Staten Island, N.Y.; Joseph A. Smith, Fanwood, N.J.

[73] Assignee: Sandoz Pharm. Corp., E. Hanover, N.J.

[21] Appl. No.: 607,251

[22] Filed: May 4, 1984

Related U.S. Application Data

[63] Continuation of Ser. No. 32,331, Apr. 23, 1979, which is a continuation-in-part of Ser. No. 745,284, Nov. 26, 1976, abandoned.

[51] Int. Cl.$^4$ .............................................. C07F 5/02
[52] U.S. Cl. ...................................... 568/1; 564/329; 252/188.1
[58] Field of Search ............................................ 568/1

[56] References Cited

U.S. PATENT DOCUMENTS 4,071,557  1/1978  Mattner .................................. 564/329
4,083,871  1/1978  Houlihan et al. ................ 564/329 X

OTHER PUBLICATIONS

Gribble et al., J. Amer. Chem. Soc. 96 (25), pp. 7812-7814 (1974).
Gribble et al., Synthesis pp. 650-652 (1975).
Chemical Abstracts 87 184194s (1977).

Primary Examiner—Helen M. S. Sneed
Attorney, Agent, or Firm—Gerald D. Sharkin; Richard E. Vila

[57] ABSTRACT

Amines are substituted, e.g. alkylated, by reacting the unsubstituted amine with a ketone or aldehyde, a borohydride and a rigid acid.

2 Claims, No Drawings

PREPARATION OF SUBSTITUTED AMINES

This is a continuation of application Ser. No. 32,331, filed Apr. 23, 1979, which in-turn is a continuation-in-part of Ser. No. 745,284, filed Nov. 26, 1976, now abandoned.

It has been previously found that amines can be substituted by reacting with a ketone or aldehyde, a borohydride and acetic acid. It was also discovered by the present applicants as described in U.S. application Ser. No. 653,361 (filed Jan. 29, 1976), now U.S. Pat. No. 4,083,871, that 2-sec-alkylaminobenzophenones could be prepared under certain controlled conditions by alkylating the corresponding 2-aminobenzophenone with a ketone in the presence of a borohydride and carboxylic acid having a pH of from 3 to 5. It was further discovered by two of the present applicants, as described in U.S. application Ser. No. 653,362 (filed Jan. 29, 1976), now U.S. Pat. No. 4,071,557, that 2-substituted aminophenyl ketones could be prepared by reacting the corresponding 2-aminophenyl ketone with a ketone or aldehyde, a borohydride and strong acid having a pH strength greater than 2.

The substitution of amines has broad application in the commercial arts and the substitution of aminophenyl ketones, especially 2-aminobenzophenones, is of considerable interest in the preparation of intermediates for pharmaceuticals. For example, the processes described in the two above-mentioned U.S. patent applications, particularly in Ser. No. 653,362, are considered to provide a substantial improvement from a cost and other standpoints in the preparation of intermediates for a new anti-inflammatory compound. However, in general, the known reactions involving the substitution of an amine with a ketone or aldehyde in the presence of a borohydride and acid have required at least a moderate excess of the borohydride which is a relatively expensive material and have left room for improvements in other aspects of the technology.

The principal object of the present invention is to provide an improved process for the substitution of amines employing a borohydride and acid, and particularly a process in which the amounts of borohydride can be reduced.

The above and other objects have now been found to be accomplished by employing in the indicated reactions certain dibasic organic acid of the rigid type, or more precisely, the reducing boron-containing salt found to result from the reaction of the rigid organic acid and a borohydride.

The borohydrides employed in the invention are those tetraborohydrides well known as reducing agents, i.e., the reducing tetraborohydrides. The particularly suitable borohydrides are the alkali metal borohydrides such as lithium borohydride, sodium borohydride, and potassium borohydride, more preferably sodium borohydride.

The rigid dibasic acids employed in the invention are those in which one or both of the two acids functions are carboxy or sulfo, ie. a —COOH and/or SO₃H function, with the two said acid functions either on adjacent carbon atoms or on carbon atoms adjacent the fused carbon atom of two fused rings, the two said acid function also being geometrically fixed in coplanar relationship, ie. in the same plane. The term "rigid" as applied to organic compounds and the influence of such rigid structures on substituents thereof are sufficiently known as to be understood by those skilled in the art. The term "rigid coplanar carboxy and/or sulfo dibasic organic acid" as used to denote the dibasic acids used in this invention will therefore also be understood with definiteness by those skilled in the art. Such dibasic acids may be divided into three main classes: (1) those acyclic compounds having a carbon to carbon double bond in which such carbon atoms each bear one of the two acid function, the geometric configuration of said carbon atom acid substituents being such as to be in the cis isomer form; (2) cyclic compounds having carbon to carbon double bond unsaturation in which two carbon atoms which are double bonded each bear one of the two acid functions and either a) the two such carbon atoms are adjacent (herein called Class 2a) or b) the two such carbon atoms are adjacent the fused carbon atom of (common to) two fused rings (herein called Class 2b); and (3) cyclic compounds in which each of two saturated ring carbon atoms bear one of the two acid functions which are fixed rigidly either endo- or exo- with respect to each by reason of the structure of the molecule. Representative of Class 1 acids is maleic acid. Representative of Class 2a acids are phthalic acid, 1,2-benzenedisulfonic acid, 2-carboxybenzenesulfonic acid, o-dicarboxynaphthalenes such as 2,3-dicarboxynaphthalene and o-disulfonaphthalene such as 2,3-disulfonaphthalene. Representative of Class 2b is bicyclo[2,2,1]hepta-5-ene-2,3-dicarboxylic acid. Representative of Class 3 is naphthalic acid. The generally preferred dibasic rigid organic acid are of Classes 1 and 2a and may be represented by the following formula I:

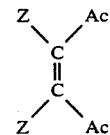

wherein each Ac independently represents —COOH or —SO₃H, each Z represents a hydrogen atom or the residue of an organic group) (preferably a hydrocarbon organic group) which may be linked to the other Z, the two Ac functions being in a cis relationship to each other. In general, the generally preferred dibasic acids are those in which the two acids functions are the same, and the more preferred acids are those in which the acid functions are both carboxy. The particularly preferred dibasic acid is phthalic acid.

Accordingly, the present invention in one of its broader aspects provides, in relation to the process of substituting primary amines involving reactively combining such an amine with an aldehyde or ketone and an acid and reducing borohydride or reaction product of said acid and borohydride, the improvement which comprises employing therein a rigid coplanar carboxy and/or sulfo dibasic organic acid or, more particularly, the reaction product of such a rigid dibasic acid and reducing borohydride, said reaction product being a boron-containing salt represented by the formula II:

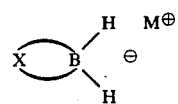

wherein X is the anionic residue of the rigid coplanar carboxy and/or sulfo dibasic organic acid (ie. such an acid less the acid hydrogen atom each of the two acid functions), and M⊕ is the equivalent of a metal cation, the term "equivalent" being used to indicate the number of metal cations or fractions thereof needed to take up one of the boron-containing anions in the salt of the formula II, such number of metal cations (one or less) being dependent upon the valence of the metal M, such valence in any event not exceeding 2, and preferably being 1. The metal M is desirably an alkali metal such as lithium, sodium or potassium, preferably sodium or potassium and more preferably sodium. The salts of the formula II are novel and represent another important aspect of the present invention.

As will be noted from formula II, the reaction of the rigid acid with the borohydride generally results in the formation of a salt having a 7 membered ring, represented in the case of phthalic acid by the salt of the formula IIa:

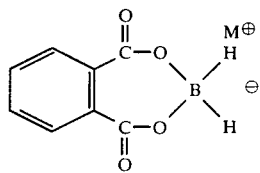

wherein M is as defined, except in the case of rigid acids of the Class 2b in which case an 8 membered ring is formed, as represented in the case of naphthalic acid by the salt of the formula IIb:

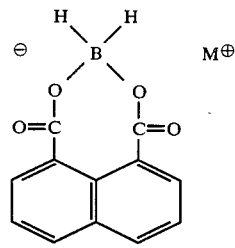

wherein M is as defined.

In general, there are two main approaches to the operation of the process of the invention, namely, in situ formation of the boron-containing salt of the formula II and ex situ formation of the salt. By in situ preparation is meant a procedure whereby the borohydride and rigid acid are reacted together in the presence of at least one other reactant required to form the desired substituted amine, and completion of the preparation of the substituted amine without isolation of the boroncontaining salt of the formula II. In general, the reaction of the salt with the amine may be carried out at temperature of from 0° C. to up any desired temperature although 100° C. represents about the upper limit for practical operation in most cases. Preferably, the reaction is carried out at from 20° C. to 85° C., more preferably, 30° C. to 65° C. The reaction temperature for preparation of the boron-containing salt from the borohydride and rigid acid may be carried out over a wide temperature range commencing at least as low as minus 40° C. and ranging up to 85° C. or more, but is preferably effected in the range of from 0° C. to 35° C., more preferably 10° C. to 30° C. In situ preparation preferably takes place in the presence of the aldehyde or ketone, desirably an excess of the amount of aldehyde or ketone theoretically required for the preparation of the substituted amine. On the other hand, ex situ preparation is desirably conducted in the presence of an inert solvent and the boron-containing salt product retained in the solvent for subsequent use.

The ratio of borohydride or boron (expressed as the borotetrahydride in in situ reactions or the boroncontaining salt in ex situ reactions) to the amine to be substituted may vary over a fairly wide range depending upon a number of factors such as yield desired, nature of the amine, reaction temperature and the like. A ratio of borohydride to amine of at least 0.7:1 is about the minimum that is practical from a yield standpoint and ratios of at least 1:1 are required theoretically for a 100 percent yield. Ratios of borohydride to amine of 2.5:1 or even greater may be employed in situations where especially rapid reactions may be desired and where the amine is otherwise completely inert to the reaction conditions or loss of yield from by-product side reactions can be tolerated or where in special cases a second reaction or modification of the amine by the borohydride may be desired. However, a major advantage of the invention is that reduced quantities of borohydride (about one half the amount) are required to effect the substitution of amines employing an acid and a ketone or aldehyde. Such advantage results in it being generally suitable to employ mole ratios of borohydride to amine of 0.7:1 to 1.65:1. Preferably; the mole ratio is from 1:1 to 1.5:1, more preferably 1:1 to 1.3:1 and desirably in the range of from 1:1 to 1.15:1. When the amount of borohydride is controlled within the advantageous range permitted by the invention (mol ratios of borohydride to amine of 0.7:1 to 1.65:1), the process of the invention also permits greater temperature flexibility where side reactions have heretofore been experienced. For example, in contrast to the processes described in the abovementioned U.S. applications Ser. Nos. 653,361 and 653,362, phenyl ketones may be substituted by the invention process at temperatures above 35° C. without substantial hydrol formation. As will be evident to those skilled in the art, operation of the process of this invention at unnecessarily high borohydride to amine ratios with amines potentially capable of borohydride reductive side reactions (such as 2-aminobenzophenones), will require the acceptance of reduced yields due to such side reactions and/or the regulation of other reaction parameters such as temperature and reaction time in order to suppress such undesired reduction reactions. Experience with the type of reductive substitution reaction in question now indicates that the reductive substitution reaction is so highly favored that amines which have a structure or bear groups known to be subject to reduction by boroncontaining reducing agents can be substituted and the desired product recovered by routinely regulating, when necessary, the relevant reaction parameters such as the borohydride ratio, temperature, time and the like. The invention is therefore applicable not only to amines which are actually otherwise inert under the reaction condition but may be applied to a wide variety of amines which are potentially not otherwise inert, eg. contain groups known to be subject to reduction by boroncontaining reducing agent. Hence, the invention process may be applied to amines generally so long as the same are otherwise substantially inert in the sense of permitting the formation of useful quantities or recovery of desired product by established procedures such as column chromatography, crystallization and the like.

IN SITU PREPARATION

In situ preparation is generally preferred and usually offers the advantage, among others, that the ketone or aldehyde can be employed as a whole or part of the solvent for the salt forming reaction. When the salt is prepared in situ it is usually more preferred to commense the salt-forming reaction at alower temperature of about 0° to 30° C., preferably 10°-25° C. by adding the borohydride to a mixture of the other reactants, and then raise the temperature slowly to preferably 30°-85° C., more preferably 40°-65° C., after an initial reaction between the borohydride and acid has taken place, in order to complete any remaining salt-forming reaction and establish conditions favoring the final substitution reaction.

A mol ratio of rigid acid to borohydride in the range of from 1:1 to 2:1 is generally preferred and a ratio of 1.1:1 to 1.8:1 is more preferred as the use of a moderate excess of rigid acid more readily assures essentially complete reaction and results in a solution in which the salt of the formula II is believed to be more stable by virtue of the additional or excess free rigid acid being present. A particularly preferred ratio is from 1.1:1 to 1.6:1. However, mol ratios as low as 0.7:1 which theoretically provide a 70% yield may be employed in in situ reactions but some loss in yield can be expected due to the observed stability factor. The upper limit on the amount of rigid acid which may be employed is not particularly critical and governed by economic considerations and the desirability of maintaining the reactants in solution. From the above it will be evident that the presence of free acid, desirably but not necessarily the rigid acid being used, although preferably a carboxylic acid, is desirable from the standpoint of preserving the boron-containing salt against the instability of salt that might be expected under basic conditions. In general, mol ratios of acid to borohydride in excess of 10:1 offer no substantial advantage and are avoided as tending to be wasteful. The borohydride is preferably employed in finely divided form, eg. as a powder.

One mol of the ketone or aldehyde, per mol of the amine represents the theoretical or stoichometric amount for the reaction. However, the reaction may be carried out employing the ketone or aldehyde to be substituted in excess as the sole solvent and/or in the presence of a variety of organic solvents including a solvent of a relatively strong polar type, eg., in the presence of such organic solvents and a stoichiometric amount of the ketone or aldehyde. In at least a practical sense, however, the process is carried out in a solution in which the solvent constitutes an excess of the ketone or aldehyde, and such exccss amounts of the ketone or aldehyde have a beneficial influence on the reaction and provide the most convenient way of achieving the desired operating conditions. For these reasons the total amount of the ketone or aldehyde is desirably an amount represented by a mol ratio to the amine of at least 3:1. The mol ratio of ketone or aldehyde to amine is more suitably at least 4:1 and preferably at least 8:1, more preferably from 10:1 to 50:1 and most usually from 15:1 to 45:1. The upper limit on the amount of the ketone or aldehyde is not critical and is more controlled by the limitations of space and other practicalities. Mol ratios to the amine in excess of 70:1 offer no prospect of additional advantages and are generally avoided. As previously indicated, other organic solvents which are inert in the sense of not having a deleterious effect on the reaction may be added, if desired, although no particular additional benefits are foreseen by reason of such addition. Such additional solvents include the common ethers and the like, such as dioxane and tetrahydrofuran. Alcohols corresponding to the ketone or aldehyde, eg. Isopropanol, may also be used. Besides the inclusion of additional solvents, the reaction mixture may contain other agents which do not have a deleterious effect on the reaction, although the reaction system preferably consists of the amine, the ketone or aldehyde, the rigid acid and the borohydride. Small amounts of water may be present in the reaction mixture due to their presence in commercial grades of certain starting materials and the like. However, substantial quantities of water have an adverse influence on the reaction and/or the yields obtainable thereby, and accordingly the amount of water, if any, is desirably limited to an amount not in excess of 8% by weight of the total solvent present in the reaction system (the term solvent as used in connection with this limitation excluding the portion of the aldehyde or ketone theoretically entering into the reaction to provide the desired substitution). Preferably, the amount of water does not exceed 2% by weight of the solvent and is more preferably not in excess of 0.5%. An amount of water representing 0.05 to 0.4% is typically introduced by starting materials and can usually be tolerated without significant adverse effect on the reaction. The reason for the adverse effect of large amounts of water is not precisely understood although it is believed that the known ability of the reducing borohydride to slowly react with water to produce hydrogen and a base which can then react with the rigid acid is a major factor. Extension of the reaction time to many times that ordinarily required can, however, largely overcome the adverse effects of moderate amounts of water, eg. amounts of from 0.5 to about 5% by weight of the solvent.

The reactants in in situ preparation may be combined in a variety of sequences as will occur to those skilled in the art but it is generally preferred to add the borohydride to the other necessary reactants, desirably at a lower temperature not favoring the substitution reaction, and then raise the temperature, optionally in stages, after the salt forming reaction is largely completed, to the temperatures more favorable to the substitution reaction.

EX SITU PREPARATION

The reaction conditions for ex situ preparation of the boron-containing salt of the formula II are similar to those for in situ preparation. Reaction temperatures may vary widely from minus 40° C. up to plus 85° C. or more, but are preferably in the range of from 0° C. to 35° C., more preferably 10° C. to 30° C. The ratio of rigid acid to borohydride may also vary fairly widely, eg. from 0.7:1 to 5:1, but are preferably from 1:1 to 2:1 and more preferably from 1.1:1 to 1.8:1. However, in ex situ reactions as compared with in situ reactions, it is generally convenient and desirable to employ a somewhat lower mol ratio of rigid acid to borohydride of from 1.1:1 to 1.5:1, particularly 1.1:1 to 1.3:1. As previously indicated, the reaction is carried out in the presence of an inert solvent capable of at least partially dissolving the reactants and a variety of inert solvents of conventional type may be employed. A preferred such solvent is tetrahydrofuran. The reaction is preferably effected by adding the borohydride, typically in staged portions, to a solution of the rigid acid, and regulating the addition so as to maintain the desired temperature and control of this exothermic reaction. The resulting salt of the formula II may be maintained in the solution in which it is formed and such solution used in the subsequent amine substitution reaction to the extent that the inert solvent employed does not introduce an undesirable solution or other problem in such amine substitution. In fact, analysis has indicated it to be important for good results on ex situ preparation that the resulting salt of the formula II be maintained in solution and the solution of the salt used in the subsequent amine substitution reaction. Hence, various attempts to recover the solid salt form of the formula II have revealed that said salt exhibits a certain instability at least to the extent of apparent further reaction with available dibasic acid such that any solid product finally recovered is to a high degree a boron-containing composition of substantially lower reducing capability than the salt of the formula II. When maintained in solution the reaction product of the borohydride and rigid acid is indicated to be predominantly to substantially exclusively a salt of the formula II with other boron-containing co-products or depreciation products at a sufficiently low level that the advantages of the invention may be realized in the use of such solutions as a reducing agent in amine substitution reactions. Any solids which may form during the reaction of the borohydride and rigid acid are preferably retained in the solvent solution and added along with the solution when used in the amine substitution reaction. It is also indicated as preferred to use the solution of the salt of the formula II on freshly prepared basis, and any retention of the solutions for other than use directly after preparation is desirably effected at the lower temperatures, eg. 0° C. or lower. The salt of the formula II is generally a strong reducing agent and the solution thereof may be used as such, eg. in reductions where borohydrides have been heretofore used.

In general, the reaction is carried out substantially in solution but the amount and quality of the reactants may be such that the reaction system as a whole may be suitably or advantageously a mixture or multi-phase system involving, for example, a suspension or slurry of a portion of one or more of the ingredients.

Generally preferred embodiments of particular interest include the preparation of 2-monosubstituted-aminophenyl ketones of the formula III and 2-monosubstituted aminobenzonitriles of the formula IV, as follows

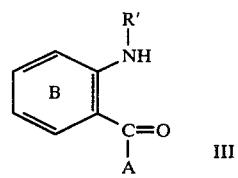 III

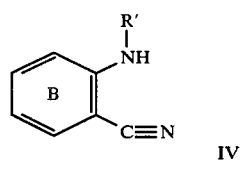 IV wherein
R' is sec.-alkyl of 3 to 7 carbon atoms, cycloalkyl of 5 to 7 carbon atoms optionally monosubstituted by alkyl of 1 to 4 carbon atoms, optionally mono- or di-substituted benzyl or optionally monosubstituted furylmethyl,
Ring B is optionally mono- or di-substituted or substituted by alkylenedioxy of 1 or 2 carbon atoms, and
A is optionally mono- or di-substituted monocyclic aryl or optionally mono- or disubstituted naphthyl;

from a corresponding 2-unsubstitutedaminophenyl ketone of the formula IIIa or 2-unsubstituted aminobenzonitrile of the formula IVa, as follows:

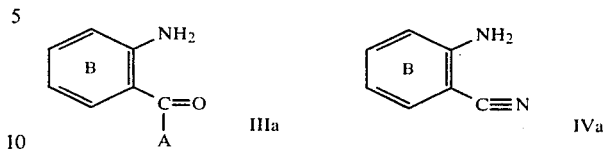

wherein A and Ring B are as above defined, and a carbonyl bearing compound (ketone or aldehyde) of the formula CB:

 CB wherein either: (1) $R_1'$ and $R_2'$ are each alkyl of 1 to 5 carbon atoms with the proviso that $R_1'$ and $R_2'$ do not exceed a total of 6 carbon atoms; (2) $R_2'$ is hydrogen and $R_1'$ is optionally mono- or di-substituted phenyl or optionally mono-substituted furyl; or (3) $R_1'$ and $R_2'$ together form an alkylene bridge of 4 to 6 carbon atoms optionally mono-substituted by alkyl of 1 to 4 carbon atoms.

When A is monocyclic aryl it is preferably phenyl, 2-thienyl, 3-thienyl, 2-furyl or 3-furyl. When A is naphthyl it may be 1-naphthyl or 2-naphthyl. When A is phenyl or naphthyl it is preferably unsubstituted, monosubstituted or disubstituted. When A is thienyl or furyl it is preferably unsubstituted or monosubstituted. Hence, the preferred significances of A may be represented by the groups of the formulae 1C-H, inclusive:

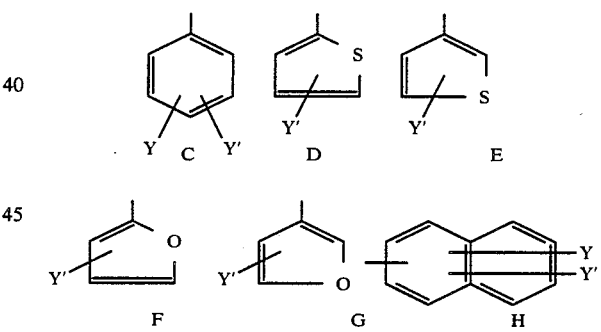

wherein Y is hydrogen, halo of atomic weight of from 18 to 80, i.e., fluoro, chloro or bromo, alkyl of 1 to 4 carbon atoms, alkoxy of 1 to 4 carbon atoms, nitro or trifluoromethyl, and Y' is hydrogen, halo of atomic weight of from 18 to 80, i.e., fluoro, chloro or bromo, alkyl of 1 to 4 carbon atoms or alkoxy of 1 to 4 carbon atoms. A is more preferably phenyl, Y-substituted phenyl, 2-thienyl or Y'-substituted 2-thienyl, and most preferably phenyl or Y-substituted phenyl, particularly phenyl or 4-fluorophenyl.

When the Ring B is substituted, the substituents are preferably one or two of the group consisting of fluoro, chloro, bromo, alkyl of 1 to 4 carbons and alkoxy of 1 to 4 carbon atoms, one of the group consisting of trifluoromethyl, alkylthio of 1 to 4 carbon atoms, nitro and cyano, or an alkylenedioxy of 1 or 2 carbon atoms, such alkylenedioxy preferably being at the 4,5-positions, more preferably 4,5-methylenedioxy.

When R' is mono- or di-substituted benzyl, the substituents are preferably fluoro, chloro, bromo, alkyl of 1 to 4 carbon atoms, alkoxy of 1 to 4 carbon atoms, alkoxy of 1 to 4 carbon atoms, nitro or trifluoromethyl. When R' is monosubstituted furylmethyl, the substituents are preferably fluoro, chloro, bromo or alkyl of 1 to 4 carbon atoms.

The reaction of the present invention is more preferably applied to the substitution of ketones and is more particularly of interest for the preparation of 2-sec.-alkylamino-benzophenones and benzonitriles of the formulae: IIIb and IVb, respectively, as follows:

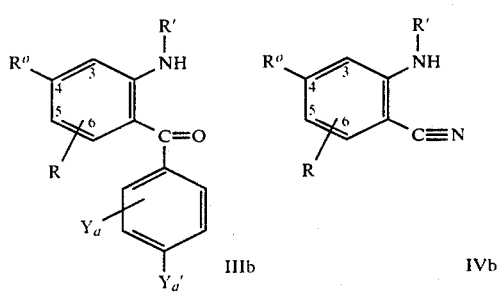

wherein
R' is a secondary alkyl of 3 to 5 carbon atoms,
R and R° are independently hydrogen, fluoro, chloro, straight chain alkyl of 1 to 4 carbon atoms, straight chain alkoxy of 1 to 4 carbon atoms or trifluoromethyl, with the provisos that R is in the 5- or 6-position, and no more than one of R and R° is trifluoromethyl, or
R° and R together form 4,5-alkylenedioxy of 1 or 2 carbon atoms, and
$Y_a$ and $Y_a'$ are independently hydrogen, fluoro, chloro, straight chain alkyl of 1 to 4 carbon atoms, straight chain alkoxy of 1 to 4 carbon atoms or trifluoromethyl, with the proviso that no more than one of $Y_a$ and $Y_a'$ is trifluoromethyl, from a corresponding 2-aminobenzophenone or 2-aminobenzonitrile of the formulae III$_c$ and IV$_c$, as follows:

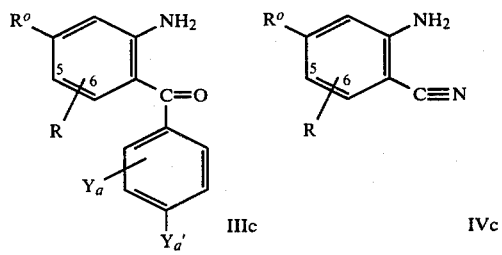

wherein R°, R, $Y_a$ and $Y_a'$ are as above defined, and a ketone of the formula:CB-I:

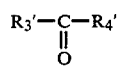
CB-I wherein $R_3'$ and $R_4'$ are each alkyl of 1 to 3 carbon atoms with the proviso that $R_3'$ and $R_4'$ do not exceed 4 carbon atoms.

The carbonyl-bearing compounds of the formula CB-I represent a generally preferred class of ketones which are most advantageously used to substitute amines by the process of the invention.

The present invention is also of interest with regard to the preparation of 2-minosubstituted-anthranilic acids and esters of the formula V:

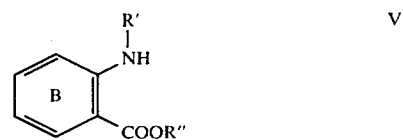

wherein R' and Ring B are as above defined and R'' is hydrogen or alkyl of 1 to 5 carbon atoms, from the corresponding 2-unsubstituted anthranilic acids and esters of the formula Va:

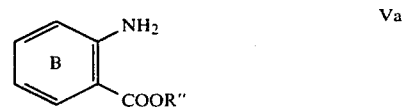

wherein Ring B and R'' are as defined.

The anthranilic acids and esters of more particular interest for preparation by the invention are of the formula Vb:

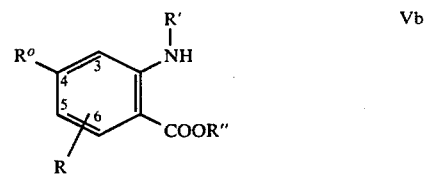

wherein R°, R, R' and R'' are as defined.

Depending upon the desired product and related factors and variables, the process of the invention affords one or more of the following savings or advantages:

(1) a substantial decrease in the amount of borohydride required to obtain equivalent yields; (2) a reduction in the batch size necessary for the reaction with its attendant advantages; (3) a more controllable, less vigorous reaction between the acid and borohydride with all of the attendant advantages; and (4) the potential for reducing environmental problems by recovery after the reaction of the rigid acid and boron in the form of boric acid.

The reaction of the present invention may be applied to substitute amines generally subject to substitution by conventional or heretofore known reductive substitution procedures, including primary and secondary amines, both cyclic and acyclic, and especially primary amines, to the extent otherwise inert under the reaction conditions, with the residue of any ketone or aldehyde. The term "residue" as applied to ketones and aldehyde refers to the radical or group formed on removal of the ketones function and the replacement of one of the two keto bonds by a hydrogen atom, eg.

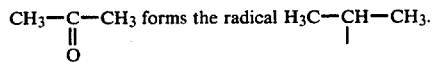

As will be appreciated, the various reactants involving the rigid acid as well as the amine to be substituted and the carbonyl bearing compound should be free of substituents and otherwise of such a structure as to be substantially otherwise inert under the reaction conditions in the sense of permitting the formation by the described reactions of at least some useful or recoverable quantity of the desired product. The ability of the described process to substitute amines of the type of formulae III, IV and V indicates the broad selectivity and applicability of the process since the compounds of said formulae contain groups known to be subject to reduction by boroncontaining reducing agents. In general, when the amine contains groups of known susceptibility to reaction with boron-containing reducing agents the potential side reactions may be suppressed by routine control and selection of reaction parameters such as temperature and boron to amine mol ratios. While greater temperature flexibility is an advantage of the invention in preparing the compounds of the formulae III, IV and V, it is generally desirable to react such compounds and others embodying potential boron-containing reducing agent induced side reactions at temperatures within the preferred temperature range of from 20° C. to 85° C., particularly from 30° C. to 65° C., and at the more practical boron to amine mol ratios of from 0.7:1 to 2.5:1, particularly from 1:1 to 1.65:1. The presence of excess acid, preferably the rigid acid employed, either in in situ reactions or by separate addition when the salt II is prepared ex situ, is also believed to favor formation of the desired product without by-product formation when substituting compounds III, IV and V and is preferred; the more preferred rigid acid to borohydride ratios, eg. 1.1:1 to 1.8:1, being representative in such cases. While we do not wish to be committed to any particular reaction mechanism, it is believed that the described process procedes in its final stage by reduction of an iminium compound (Schiff base) of the same nature postulated for the heretofore known reductive substitution reactions that employ boron-containing reducing agents.

The compounds of the formula IV and V (including IVb and Vb) may be converted (the compound V in free acid form) by known procedures involving, for example, the reaction with an aryl Grignard reagent or aryl lithium compound to the compounds of the formula III. The compounds of the formula III are interest in a variety of applications including intermediary use for preparing by cyclization compounds having pharmacological activity. For example, the compounds III may be cyclized with urea in acetic acid at 80° C. to 150° C. to produce 1-substituted-4-aryl-quinazolin-2(1H)-ones of which, for example, those in which the 4-aryl group is of the formulae C-G, as above given, are of particular interest as anti-inflammatory agents, especially those in which the 4-aryl group is of the formula C, and more particularly those prepared by cyclizing the compounds of the formula IIIb.

The following examples illustrate the present invention.

EXAMPLE 1

Preparation of 2-(N-isopropylamino)-4-methylbenzophenone.

422.6 g. (2 moles) of 2 amino-4-methylbenzophenone is dissolved in 2.34 liters (40.29 moles) of acetone, and with stirring 540 gms (3.25 moles) of o-phthalic acid is added. To the resulting suspension is added portionwise 80 gms (2.14 moles) of sodium borohydride over a period of 45 minutes and in a manner such as to keep the reaction mixture at 20°-25° C. At the end of the addition, the cooling is altered such as to allow the temperature to rise to 30°-35° C., and this temperature is maintained for 30 minutes. The cooling is removed and the temperature carefully increased to 50° C., and regulated at 50°-55° C. for 90 minutes. The mixture is then cooled to 15° C., 808 gms of 8% aqueous NaOH (1.625 moles) is added, the phases separated and the acetone phase (upper layer) recovered and concentrated. The water layer is extracted with 1 litre of heptane, and the concentrated acetone phase added to the heptane extract. The heptane solution is washed with 250 mls of H₂O, then concentrated by distillation to obtain 496 gms of 2-(N-isopropylamino)-4-methylbenzophenone, b.p. 180°-185° C./5mm (Yield 99%).

EXAMPLE 2

Preparation of 2-isopropylamino-4-methylbenzonitrile

To a stirred mixture of 264 g. of 2-amino-4methylbenzonitrile, 504 g. of phthalic acid and 2.32 liters of reagent grade acetone is added 80 g. of sodium borohydride portionwise over 40 minutes at a temperature of 18°-30° C. The resulting solution is stirred for 30 minutes during which the temperature rises from 29°-30° C. to 35° C. and then dropped to 34° C. The resulting solution is then heated from 34° C. to 53° C. over a period of 30 minutes and their maintained at 55° C. for one hour. The mixture is cooled to 37° C., 500 ml. of water added followed by addition of 417 g. of 50% aqueous sodium hydroxide, after which the temperature is allowed to rise to 56° C. to maintain the solution. An additional 92 ml. of water is added and the acetone and aqueous salt layers separated at 45°-50° C. The acetone layer is concentrated in vacuo to obtain a brown oil and salt solution which is diluted with 800 ml. of heptane and the aqueous and heptane layers separated. The heptane layer is dried, filtered and cooled to 10° C. to obtain the major portion of the desired 2-isopropylamino-4-methylbenzonitrile, m.p. 55°-57° C. Additional product is also recovered from the mother liquor and phthalic acid is recovered to a high degree from aqueous salt layer above referred after dilution with a total of 4.5 liters of water, filtering and acidifying with sulfuric acid (other aqueous alkaline solutions obtained in the work up being combined with said aqueous salt layer).

EXAMPLE 3

Sodium dihydro(phthalato)borate(1-)

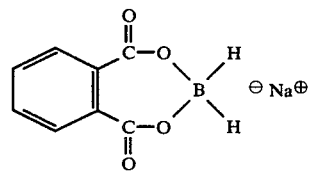

To a stirred solution of 10.8 g. of phthalic acid in 100 ml. of tetrahydrofuran is added portionwise 1.6 g. of powdered sodium borohydride over a period of 5 minutes at 25°-30° C. under ice cooling. The resulting mixture is stirred at 25° C. for 16 hours, to obtain a solution of the desired sodium dihydro (phthalato)borate (1−).

EXAMPLE 4

The procedure of Example 3 is repeated except that the amount of phthalic acid is reduced to 1.15 g. to again obtain a solution of the sodium dihydro(phthalato) borate (1−).

EXAMPLE 4A

The solutions produced in both Example 3 and 4 produced 2-isopropylaminobenzophenone when added on a freshly prepared basis (within 2 hours after preparation) to a mixture of 2-aminobenzophenone and acetone at 30°–35° C.

EXAMPLE 4B

The solution produced in Examples 3 and 4 are filtered and the filtrate concentrated to a solid weighing 15.2 g. which is triturated with chloroform, filtered and dried under vacuum at 60° C. with a nitrogen sweep. The two resulting solid products when added to a mixture of 2-aminobenzophenone and acetone at 30°–35° C. both produce 2-isopropylaminobenzophenone but in minor yield.

EXAMPLE 5

Repeating substantially the reaction procedure of Example 1 but replacing the 2-amino-4-methylbenzophenone with a molar equivalent amount of a) aniline; and b) butylamine, there is obtained respectively: a-1) N-isopropylaniline; and b-1) N-isopropylbutylamine.

EXAMPLE 6

The reaction procedure of Example 1 is repeated except that the acetone is replaced by a molar equivalent amount of benzaldehyde and 750 ml. of isopropanol is added to obtain 2-benzylamino-4-methylbenzophenone.

EXAMPLE 7

Following the reaction procedure of Example 1 and substituting the appropriate starting material in molar equivalent amount there is also obtained:
 (a) 2-(N-isopropylamino)-5-chlorobenzophenone.
 (b) 2-(N-isopropylamino)-4,5-methylenedioxy-4'-fluorobenzophenone, and
 (c) 2-(N-isopropylamino)phenyl-2-thienyl ketone.

EXAMPLE 8

N-Isopropylanthranilic acid

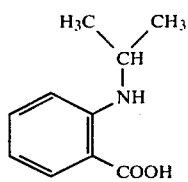

To stirred mixture of 2.7 g. of anthranilic acid and 5.4 g. of phthalic acid in 23 ml. of acetone is added 0.7 g. of powdered sodium borohydride over a period of 30 minutes at 20° C.–30° C. The resulting slurry is then stirred at 35°–40° C. for 4 hours, diluted with 25 ml. of chloroform and filtered. The filtrate is concentrated in vacuo and the residue dissolved in 20 ml. of chloroform and treated with 30 ml. of hexane, filtered and the filtrate concentrated in vacuo to obtain a crude solid product which is recrystallized 5 times from cyclohexane to obtain (second crop of fifth recrystallization) N-isopropylanthranilic acid, m.p. 109°–109.5° C.

EXAMPLE 9

Following the reaction procedure of Example 8 but substituted a molar equivalent amount of anthranilic acid ethyl ester for the anthranilic acid, there is obtained N-isopropylanthranilic acid ethyl ester.

What is claimed is:

1. A composition comprising an organic solvent having dissolved therein a boron-containing reducing agent which is a salt of the formula:

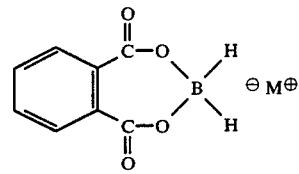

wherein M is the equivalent of an alkali cation.

2. A composition in accordance with claim 1 in which M is sodium.

* * * * *